United States Patent [19]

Miner

[11] Patent Number: 4,833,133
[45] Date of Patent: May 23, 1989

[54] METHOD OF REGULATING FERTILITY IN CATTLE USING EPOSTANE

[75] Inventor: William S. Miner, Naperville, Ill.

[73] Assignee: Sterling Drug Inc., New York, N.Y.

[21] Appl. No.: 866,009

[22] Filed: May 22, 1986

[51] Int. Cl.$^4$ .............................................. A61K 31/58
[52] U.S. Cl. .................................................. 514/172
[58] Field of Search ........................................ 514/172

[56] References Cited

U.S. PATENT DOCUMENTS

| | | | |
|---|---|---|---|
| 4,029,776 | 6/1977 | Cafruny et al. | 514/172 |
| 4,061,733 | 12/1977 | Gunjikar | 514/239.2 |
| 4,062,954 | 12/1977 | Potts | 514/172 |
| 4,160,027 | 7/1979 | Christiansen | 424/241 |
| 4,717,569 | 1/1988 | Harrison et al. | 514/172 |

FOREIGN PATENT DOCUMENTS 2155018 9/1985 United Kingdom ................ 514/172

OTHER PUBLICATIONS

Nutrient requirements of domestic animals, No. 3, Nutrient requirements of dairy cattle, 5th revised edition, 1978.
1986 USAN and the USP dictionary of drug names, 1961–1985 cumulative list, title page and p. 126.
Ledger et al., Journal of Steroid Biochemistry, vol. 17, no. 3, p. xci abst. 271, 1982.
Blackwell master of science degree thesis at New Mexico State University Las Cruces, New Mexico, 1984; title page, pp. i–xii and pp. 1–48.
Ledger et al., Journal of Endocrinology, vol. 105, pp. 227–233, 1985.
Webb, Arthur Walpole Memorial Lecture for the Society for the Study of Fertility, University of Aberdeen, 1985, pp. 1–11 and 2 fig.

*Primary Examiner*—Donald G. Daus
*Assistant Examiner*—Cecilia Shen
*Attorney, Agent, or Firm*—Theodore C. Miller; Paul E. Dupont

[57] ABSTRACT

The method of regulating fertility in cattle which comprises administering to a normally cycling cow in the early luteal phase of the cycle an amount of epostane sufficient to induce estrus is disclosed.

6 Claims, No Drawings

METHOD OF REGULATING FERTILITY IN CATTLE USING EPOSTANE

BACKGROUND OF THE INVENTION

1. Field of the Invention

The invention relates to a method of regulating fertility in cattle using epostane.

2. Information Disclosure Statement

Epostane is the United States Adopted Name (1986 USAN and the USP dictionary of drug names, 1961–1985 cumulative list) for $(4\alpha,5\alpha,17\beta)$-4,5-epoxy-3,17-dihydroxy-4,17-dimethylandrost-2-ene-2-carbonitrile having the structural formula

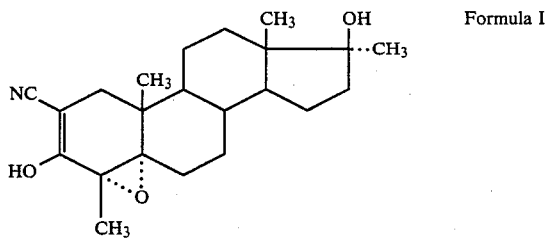

Formula I and having utility as an interceptice (pregnancy disrupting) agent.

Christiansen U.S. Pat. No. 4,160,027 issued July 3, 1979 describes epostane as the product of part (f) of EXAMPLE 1, that is, $4\alpha,5\alpha$-epoxy-$17\beta$-hydroxy-4,17-dimethyl-3-oxoandrostane-$2\alpha$-carbonitrile having the structural formula

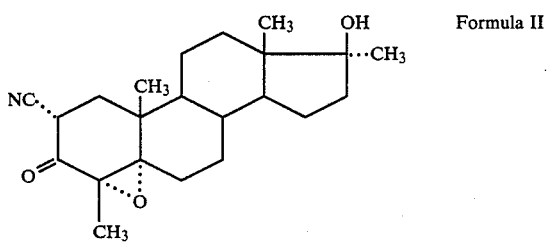

Formula II which represents the keto form of epostane. Formula I represents the enol form. The patent shows the interceptive utility of epostane in the rat and the monkey.

The only domestic animal in which the use of epostane has been described is the sheep.

A Ledger et al. (Journal of Steroid Biochemistry, vol. 17, no. 3, p. xci, abst. 271, 1982) paper entitled THE SUCCESS OF LABOUR INDUCED BY PROGESTERONE WITHDRAWAL IN PREGNANT SHEEP describes the use of epostane "to induce labour in sheet during late pregnancy".

The master of science in animal science degree thesis of Jeffrey A. Blackwell (New Mexico State University, Las Cruces, N.M., 1984) entitled REPRODUCTIVE PERFORMANCE OF EWES TREATED WITH AN INHIBITOR OF PROGESTERONE SYNTHESIS describes the effects of epostane medication at day 10 of the estrus cycle in cycling ewes, specifically, serum progesterone levels, recycling time, conception rate and number of lambs produced.

A second Ledger et al. paper (Journal of Endocrinology, vol. 105, pp. 227–233, 1985) describes the "effects of an inhibitor of $3\beta$-hydroxysteroid dehydrogenase (epostane) on uterine activity and cervical softening . . . in eight sheep during late pregnancy".

The Arthur Walpole Memorial Lecture for the Society for the Study of Fertility by Robert Webb (University of Aberdeen, 1985) describes the effects of epostane on ovulation rate and production of lambs in ewes.

SUMMARY OF THE INVENTION

The invention is the method of regulating fertility in cattle which comprises administering to a normally cycling cow in the early luteal phase of the cycle an amount of epostane sufficient to induce estrus.

DETAILED DESCRIPTION OF THE INVENTION INCLUSIVE OF THE PREFERRED EMBODIMENTS

In order to reduce costs in raising cattle there is a need to control the timing of estrus in cows so that they can be bred with greater control. The presently described and claimed invention fulfills that need.

The term "cattle" refers to both dairy cattle and beef cattle. A "normally cycling cow" is one which is nonpregnant. The day on which estrus is first evidenced by overt signs, that is, clear vaginal mucus, an erect uterus and/or appearance of a follicle on an ovary, is considered to be day 0 of the cycle. Ovulation normally occurs on day 1–2. The luteal phase normally lasts from day 2 through day 21. Estrus normally recurs after day 21. The term "early luteal phase" refers to days 2 through 10.

Any amount of epostane sufficient to induce estrus can be used. The preferred dose is from about 1 mg./kg. to about 20 mg./kg. per day or from about 0.5 g./cow to about 10 g./cow per day, for from one to five consecutive days. Ideally the overt signs of estrus appear on the day following completion of medication, insemination is allowed to take place naturally or is carried out artificially, and the cow is impregnated. Experimentally the serum progesterone concentration is measured to confirm estrus and in the event an overt sign of estrus does not appear. The serum progesterone concentration rises from about 5 ng./ml. to about 7 ng./ml. during the luteal phase of the cycle and falls to less than 1 ng./ml. during natural estrus or during estrus induced by epostane. Accordingly, a serum progesterone concentration of less than 1 ng./ml. is considered to be an indicator of estrus absent an overt sign of estrus.

The epostane can be prepared for administration in any pharmaceutically acceptable oral, vaginal, rectal or parenteral dosage form. The oral dosage form can be solid or liquid and can be capsule, tablet, solution, suspension or emulsion. The vaginal or rectal dosage form is preferably the suppository. The parenteral dosage form can be solution, suspension or emulsion. An oral dosage form is preferred. Capsules are particularly preferred.

Two studies were carried out. In the first study three cows were used in five experiments. The dose of epostane was 2.5 g./cow per day for two consecutive days orally as an encapsulated dry powder. In the second study three cows were used. Each was medicated orally with 5 mg./kg. of epostane per day for four days at noon on days 8–11 of the cycle.

In the first experiment with the first cow in the first study the 2.5 g. doses of epostane were given at 8:00 a.m. on days 9 and 10. A corpus luteum was palpated on the right ovary on days 6 and 9 and was detected to be receding on day 10. On day 11 clear vaginal mucus and an erect uterus were observed as overt signs of estrus. On day 12 there were no overt signs of estrus and the cow was pastured with a bull. On day 19 the cow was not attractive to the bull, and on that day and day 30 a corpus luteum was palpated on the right ovary. On day 50 the cow was determined to be 30-40 days pregnant. Table 1-1-1 (first study - first cow - first experiment) shows the serum progesterone concentrations determined in this experiment.

TABLE 1-1-1

| Day of Cycle | Time of Day | Progesterone Concentration (ng./ml.) |
| --- | --- | --- |
| 6 | a.m. | 2.6 |
| 9 | a.m. | 4.2 |
| 10 | a.m. | 0.9 |
|  | p.m. | 0.8 |
| 11 | a.m. | 1.17 |
| 12 | a.m. | 2.7 |
| 19 | a.m. | 4.7 |
| 30 | a.m. | 6.1 |
| 50 | a.m. | 9.8 |

In the second experiment with the second cow in the first study the 2.5 g. doses of epostane were given at noon of day 7 and 8 a.m. of day 8. A corpus luteum was palpated on the right ovary on day 7. Although no overt sign of estrus appeared, occurrence of estrus was deduced from the serum progesterone concentration on day 8. On day 9 the cow was pastured with a bull. Impregnation did not occur and on day 31 estrus recurred. Table 1-2-2 shows the serum progesterone concentrations determined in this experiment.

TABLE 1-2-2

| Day of Cycle | Time of Day | Progesterone Conentration (ng./ml.) |
| --- | --- | --- |
| 0 | a.m. | <0.3 |
| 7 | a.m. | 2.9* |
| 8 | a.m. | 0.7 |
| 9 | a.m. | 0.9 |
| 21 | a.m. | 3.9 |
| 31 | a.m. | <0.6 |

*Before medication with epostane

In the third experiment with the second cow in the first study the 2.5 g. doses of epostane were given at 8 a.m. on days 5 and 6. A corpus luteum was palpated on the right ovary on day 5. On days 10 and 11 vaginal mucus and a follicle on the left ovary appeared as overt signs of estrus and the cow was artificially inseminated. No overt sign of estrus was evident on day 31, but the serum progesterone concentration was determined to be 0.3 ng./ml. On day 39 a corpus luteum appeared on the right ovary, and the cow was not pregnant. Table 1-2-3 shows the serum progesterone concentrations determined in this experiment.

TABLE 1-2-3

| Day of Cycle | Time of Day | Progesterone Concentration (ng./ml.) |
| --- | --- | --- |
| 0 | a.m. | <0.3 |
| 5 | a.m. | 2.3* |
| 6 | a.m. | 0.8 |
| 10 | a.m. | <0.3 |
| 21 | a.m. | 1.1 |
| 31 | a.m. | 0.3 |
| 39 | a.m. | 5.6 |

*Before medication with epostane

In the fourth experiment with the second cow in the first study the 2.5 g. doses of epostane were given at 8 a.m. on days 8 and 9. On day 8 a corpus luteum was palpated on the left ovary. The cow was artificially inseminated on days 12 and 13 but underwent estrus on day 19. Table 1-2-4 shows the serum progesterone concentrations determined in this experiment. The return of the serum progesterone concentration to premedication level on day 13 and the occurrence of estrus on day 19 both evidence incomplete interruption of the luteal phase in this experiment.

TABLE 1-2-4

| Day of Cycle | Time of Day | Progesterone Concentration (ng./ml.) |
| --- | --- | --- |
| 8 | a.m. | 3.8* |
|  | p.m. | 0.5 |
| 9 | a.m. | 0.5 |
|  | p.m. | 0.4 |
| 13 | a.m. | 3.7 |

*Before medication with epostane

In the fifth experiment with the third cow in the first study the 2.5 g. doses of epostane were given at 8:00 a.m. on days 7 and 8. The uterus was erect and a follicle was detected on the left ovary on day 0. Vaginal bleeding was observed on day 1. On day 7 a corpus luteum was palpated on the left ovary. Artificial insemination was carried out on day 12, but estrus and vaginal bleeding occurred on day 20. Table 1-3-5 shows the serum progesterone concentrations determined in this experiment. The rapid return of the serum progesterone concentrations to premedication levels on days 8, 10 and 12 and the occurrence of estrus on day 20 both evidence incomplete interruption of the luteal phase in this experiment.

TABLE 1-3-5

| Day of Cycle | Time of Day | Progesterone Concentration (ng./ml.) |
| --- | --- | --- |
| 0 | a.m. | 0.2 |
| 1 | a.m. | <0.3 |
| 7 | a.m. | 2.3* |
| 8 | a.m. | 0.8 |
|  | p.m. | 2.3 |
| 10 | a.m. | 2.5 |
| 12 | a.m. | 2.9 |
| 20 | a.m. | <0.3 |

*Before medication with epostane

In the second study in all three cows luteolysis occurred 2-3 days after start of treatment, that is, on days 10-11 of the cycle, and ovulation occurred 4-5 days after start of treatment, that is, on days 12-13 of the cycle. In one of the cows, which was typical of the three, the serum progesterone concentration rose about linearly from about 0.2 ng./ml. (the assay limit) on day 2 to about 6.5 ng./ml. on day 8, fell precipitously to about 1.5, then about 1.0, then about 0.8 ng./ml. on day 9, to the assay limit on day 10, remained at the assay limit from day 10 through day 18, rose about linearly from the assay limit on day 18 to about 13 ng./ml. on day 28, and fell to about 7 ng./ml. on day 30. These results show a serum progesterone concentration indicative of estrus beginning on day 9. Accordingly, the medications on days 10 and 11 might have been necessary.

I claim:

1. The method of regulating fertility in cattle which comprises administering to a normally cycling cow during days 2-11 of the cycle an amount of epostane sufficient to induce estrus.

2. The method according to claim 1 wherein the amount of epostane is from about 1 mg./kg. to about 20 mg./kg. per day or from about 0.5 g./cow to about 10g./cow per day.

3. The method according to claim 2 wherein the epostane is administered for from one day to five consecutive days.

4. The method according to claim 3 wherein the epostane is administered orally.

5. The method according to claim 4 wherein the amount of epostane is about 2.5 g./cow per day for two consecutive days.

6. The method according to claim 4 wherein the amount of epostane is about 5 mg./kg. per day for four consecutive days.

* * * * *